(12) United States Patent
Koehler et al.

(10) Patent No.: US 12,102,467 B2
(45) Date of Patent: Oct. 1, 2024

(54) LUNG VOLUME ESTIMATION FROM RADIOGRAPHIC IMAGES

(71) Applicant: KONINKLIJKE PHILIPS N.V., Eindhoven (NL)

(72) Inventors: Thomas Koehler, Norderstedt (DE); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/279,479

(22) PCT Filed: Dec. 16, 2022

(86) PCT No.: PCT/EP2022/086339
§ 371 (c)(1),
(2) Date: Aug. 30, 2023

(87) PCT Pub. No.: WO2023/117753
PCT Pub. Date: Jun. 29, 2023

(65) Prior Publication Data
US 2024/0081769 A1     Mar. 14, 2024

(30) Foreign Application Priority Data
Dec. 20, 2021   (EP) ..................................... 21216069

(51) Int. Cl.
*A61B 6/50*     (2024.01)
*A61B 6/00*     (2006.01)

(52) U.S. Cl.
CPC .............. *A61B 6/5235* (2013.01); *A61B 6/50* (2013.01)

(58) Field of Classification Search
None
See application file for complete search history.

(56) References Cited

U.S. PATENT DOCUMENTS 9,117,287 B2    8/2015  Masumoto
9,339,243 B2 *  5/2016  Zhang .................. A61N 5/1049
(Continued)

FOREIGN PATENT DOCUMENTS

CN    107665497 A    2/2018
CN    111652924 A    9/2020
(Continued)

OTHER PUBLICATIONS

PCT International Search Report, International application No. PCT/EP2022/086339, Apr. 13, 2023.
(Continued)

*Primary Examiner* — Idowu O Osifade
(74) *Attorney, Agent, or Firm* — Larry Liberchuk

(57) ABSTRACT

There is provided a computer-implemented method of estimating lung volume from radiographic images. The method comprises: registering (102) a two dimensional radiographic image (12) of a patients chest to a three dimensional radiographic image (14) of the patients chest to estimate data describing projection geometry (16) of an imaging setup used to capture the two dimensional radiographic image; using the projection geometry to estimate (104) at least one radiographic magnification factor (18) relating to the imaging setup; and calculating (106) an estimated lung volume (20) using the two dimensional radiographic image and the at least one radiographic magnification factor.

14 Claims, 14 Drawing Sheets

(56) References Cited

U.S. PATENT DOCUMENTS

| | | | |
|---|---|---|---|
| 9,805,467 B2 | 10/2017 | Maack | |
| 2006/0274145 A1* | 12/2006 | Reiner | G16H 30/20 |
| | | | 707/E17.031 |
| 2014/0334709 A1 | 11/2014 | Siewerdsen | |
| 2016/0210739 A1 | 7/2016 | Maack | |
| 2018/0005374 A1 | 1/2018 | Kasai | |
| 2018/0271465 A1 | 9/2018 | Proks | |
| 2019/0328346 A1 | 10/2019 | Kasahara | |
| 2020/0065984 A1 | 2/2020 | Ketcha | |
| 2021/0137634 A1* | 5/2021 | Lang | A61B 5/113 |
| 2022/0087624 A1* | 3/2022 | Quinlan | A61B 6/4417 |

FOREIGN PATENT DOCUMENTS

| | | |
|---|---|---|
| EP | 3788959 A1 | 3/2021 |
| WO | WO2014202705 A1 | 12/2014 |
| WO | WO2019236317 A1 | 12/2019 |
| WO | WO2020043585 A1 | 3/2020 |

OTHER PUBLICATIONS

Weese et al., "Voxel-Based 2-D/3-D Registration of Fluoroscopy Images and CT Scans for Image-Guided Surgery", IEEE Transaction on Information Technology in Biomedicine, vol. 1, No. 4, pp. 284-293, Dec. 1997.

Yang, H. et al., "Geometry Calibration Method for a Cone-Beam CT System", Medical Physics, vol. 44, Issue 5, pp. 1692-1706, May 2017.

* cited by examiner

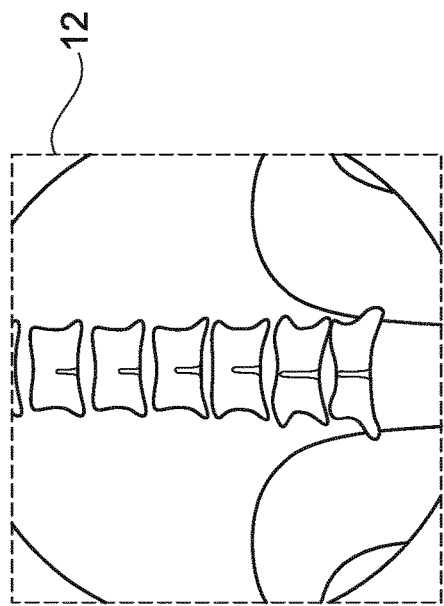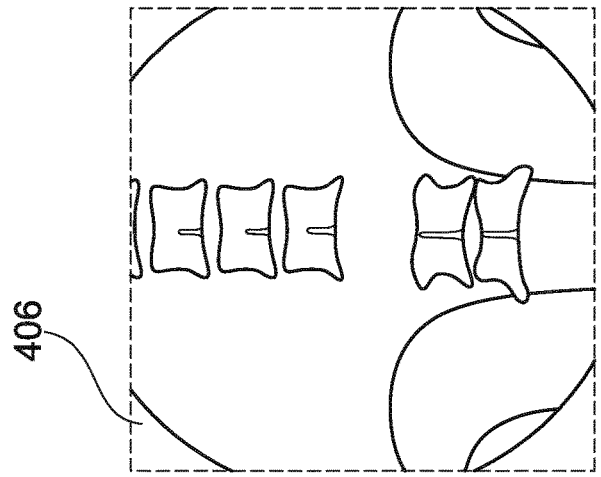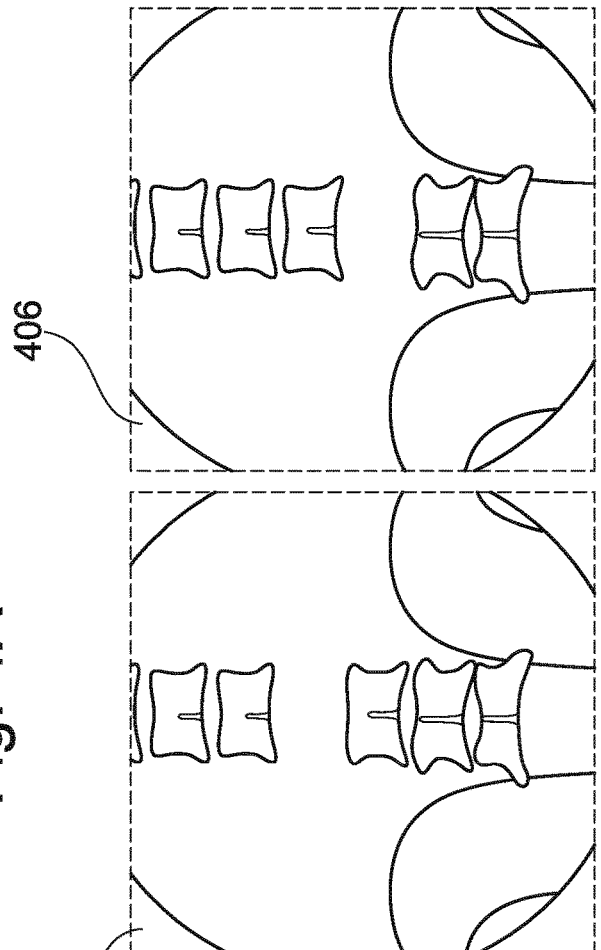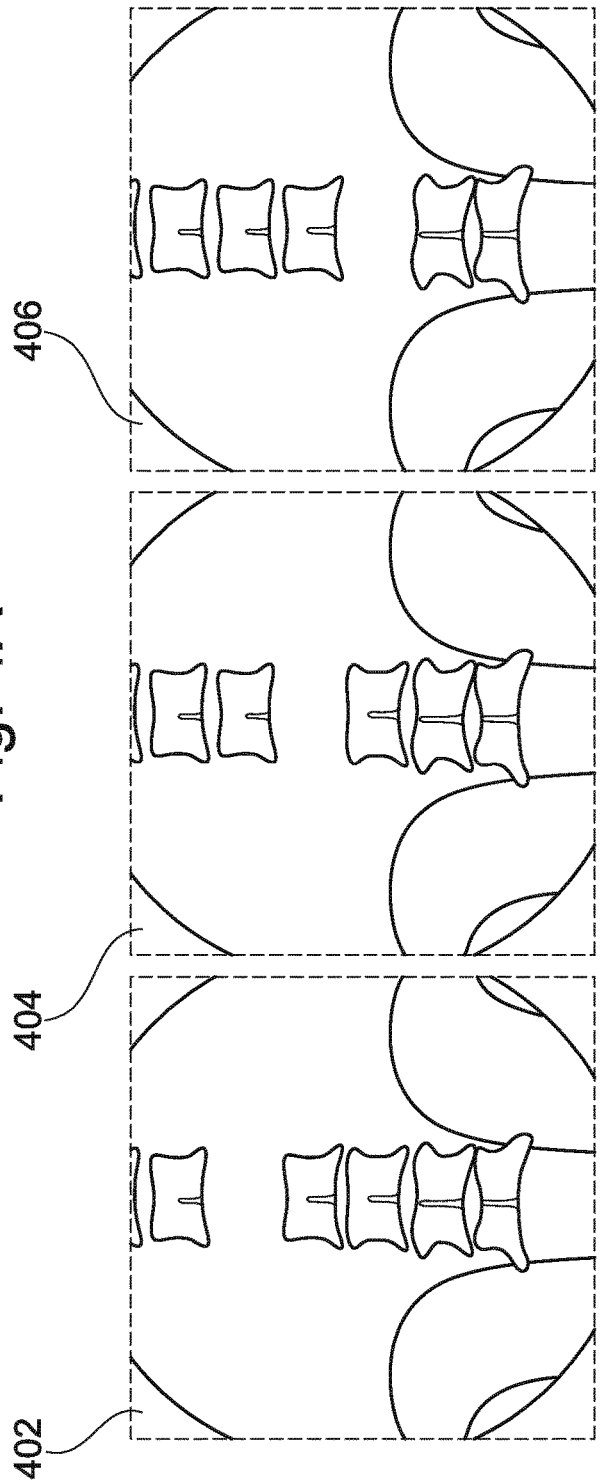

LUNG VOLUME ESTIMATION FROM RADIOGRAPHIC IMAGES

FIELD OF THE INVENTION

The invention relates to systems and methods for estimating lung volume from radiographic images.

BACKGROUND OF THE INVENTION

X-ray imaging is a standard tool for tracking the status of the lung in the intensive care unit (ICU). Often, an x-ray is taken every other day in order to assess changes of the lung, in particular to look for pleural effusion, atelectasis, and the like. It has been proposed recently to move towards a quantitative evaluation of the x-ray images with respect to total air volume in the lungs, to provide more reliable information about the patient's status. Lung volume estimation from a single x-ray image requires knowledge about the projection geometry. However, x-rays are often taken by manually placing a mobile detector below the patient in or below the bed, such that there is no fixed source-detector distance. Furthermore, the positioning of the patient may change due to other requirements, for instance to ventilate the patient in a prone position, or in a supine one. Such changes in the projection geometry present challenges for accurate lung volume estimation.

SUMMARY OF THE INVENTION

To better address one or more of these concerns, in a first aspect of invention there is provided a computer-implemented method of estimating lung volume from radiographic images. The method comprises: registering a two dimensional radiographic image of a patient's chest to a three dimensional radiographic image of the patient's chest to estimate data describing projection geometry of an imaging setup used to capture the two dimensional radiographic image; using the projection geometry to estimate at least one radiographic magnification factor relating to the imaging setup; and calculating an estimated lung volume using the two dimensional radiographic image and the at least one radiographic magnification factor.

Registering the two dimensional (2D) radiographic image and the three dimensional (3D) radiographic image may be performed using at least one trained machine learning model. Additionally or alternatively, the registration may be performed using at least one computational or geometric registration algorithm.

At least one trained machine learning model may be used to register the 2D image to the 3D image to estimate the data describing the projection geometry.

In one example, the geometric registration algorithm comprises an intensity-based registration algorithm which compares intensity patterns in the two images via one or more correlation metrics. For example, the geometric registration algorithm may be based on minimizing an intensity similarity measure between both images while varying pose parameters. Additionally or alternatively, the registration algorithm may comprise a feature-based registration algorithm which finds correspondence between one or more image features such as points, lines, and contours.

The registration may register the 2D and 3D images in their entirety or may use sub-images of one or both of the 2D and 3D images. The registering may thus comprise forming a sub-image from one or both of the 2D and 3D images before performing the registration. If sub-images are registered, the sub-images may depict at least one anatomical structure to be used in the registration, i.e. at least one object of interest. In one particular non-limiting example, the at least one anatomical structure comprises one or more vertebrae. Additionally or alternatively, the at least one anatomical structure may comprise one or more ribs. The sub-images may be formed or created by segmenting the 2D and 3D images to isolate the at least one anatomical structure, for example to segment at least one vertebra. Thus, the 2D image may be segmented to identify a region of interest depicting the anatomical structure, while the 3D image may be segmented to identify a volume of interest depicting that same anatomical structure.

The registration algorithm may comprise an iterative registration algorithm. Thus, in one example, comparing intensity patterns in the two images may comprise using an iterative registration algorithm which repeatedly makes incremental changes to an estimated projection geometry and calculates the correlation metric between the two images being registered using the incrementally-changed projection geometry until the correlation metric converges to a steady state value. The steady state value may be a maximum or optimal value. Thus, the method may comprise using an optimization algorithm to maximize the correlation metric. To compare the 2D image with the 3D image, the method may comprise first reconstructing a 2D image from the 3D image, using for example the estimated projection geometry selected for the current iteration. The method may comprise subtracting the reconstructed 2D image (that which is computed from the 3D image) from the 2D image before calculating the correlation metric. The iterative algorithm may use predetermined starting estimates for the projection geometry, and/or predetermined increment sizes, and/or a predetermined order in which the parameters of the projection geometry are incremented. The correlation metric may comprise a similarity metric which quantifies the degree of similarity between intensity patterns in the two images. In one particular non-limiting example, the similarity metric describes the structuredness of a difference image which is obtained by subtracting one of the two images being registered from the other. Other examples of suitable similarity metrics include cross-correlation, mutual information, sum of squared intensity differences, and ratio image uniformity.

The method may comprise preprocessing one or both of the two images before performing the registration. For example, one or both of the images may be preprocessed to adjust grey-scale variation, for example by removing an average grey value from a region outside of the object of interest, and/or by applying one or more scaling factors.

The projection geometry may be described by a transformation, i.e. a geometric transformation, which may for example relate the different coordinate systems used by the 2D and 3D images, so as to map one of the images to the other. The transformation may be represented by one or more transformation parameters, such as rotation and translation parameters. In one example, up to nine parameters may be used to represent the projection geometry: three for the position of the source, three for the position of the detector, and three for the orientation of the detector or detector plane. Constraints imposed by the imaging setup, e.g. a fixed source-detector distance or a source mounting which is rotatable about fewer than three axes, may allow fewer than nine parameters (i.e. a subset of parameters) to be used to represent the projection geometry fully.

In one example, the magnification factor for at least one lung may be estimated using at least a source-lung distance. More particularly, the magnification factor of the lung may be calculated as the ratio of a source-lung distance over a source-detector distance (i.e. the sum of the source-lung distance plus a lung-detector distance). Yet more particularly, the magnification factor for the lung may be calculated as $$M = \frac{\overline{SL}}{\overline{SL} + \overline{LD}},$$

where $\overline{SL}$ and $\overline{LD}$ are the source-lung and lung-detector distances, respectively, for the lung in question. These distances may be measured on a straight line passing from the source, through the centre of the lung in question, to the detector.

In another example, the magnification factor for at least one lung may be estimated using at least a source-anatomy distance (e.g. a distance between the x-ray source and an anatomical structure used in the image registration, together with a lung-anatomy distance (e.g. a distance between the lung or lungs and the said anatomical structure). Using the lung-anatomy distance in the calculation may comprise using knowledge of a position (e.g. a prone or supine) in which the patient was lying when the 2D image was captured, for example to select an appropriate estimation method. In other words, the method may comprise applying the lung-anatomy distance differently according to whether the patient is in a supine or prone position. More particularly, the magnification factor for the lung or lungs may be estimated as $$M = \frac{\overline{SD}}{\overline{SV} - \overline{LV}},$$

it the patient is in a supine position, or $$M = \frac{\overline{SD}}{\overline{SV} + \overline{LV}},$$

if the patient is in a prone position, where $\overline{SD}$ is the source-detector distance, $\overline{SV}$ is the source-anatomy distance (for example a source-vertebra distance between the source and the vertebra, e.g. the vertebral plane found in the image registration), and $\overline{LV}$ is the lung-anatomy distance (for example a lung-vertebra distance between the vertebra or vertebral plane and the lung mid-plane).

Estimating the at least one radiographic magnification factor may comprise estimating a magnification factor for at least one lung, for example for one or both lungs if the same magnification factor applies to both, or for each lung separately if different magnification factors apply. The magnification factor may be different for the left and the right lung if the patient is placed obliquely in the beam, that is, if the midpoints or centres of the two lungs are not equidistant from the detector plane. In the above-mentioned calculations, a single source-lung distance $\overline{SL}$, a single lung-detector distance $\overline{LD}$, or a single lung-anatomy distance $\overline{LV}$ may be used in the case that the volume of only one lung is being estimated, or these values may be taken to apply to both lungs when both lungs are equidistant from the source. Otherwise, for example in the case that the patient is lying in an oblique position, estimating the at least one radiographic magnification factor may comprise estimating magnification factors individually for the left and/or right lungs. More particularly, separate source-lung distances, lung-detector distances, and/or lung-anatomy distances may be obtained for the left and right lungs and per-lung magnification factors estimated by substituting these values into the above equations. Moreover, a magnification factor relating to the at least one anatomical structure, e.g. a vertebra, may be calculated, for example as $$M_V = \frac{\overline{SD}}{\overline{SV}}.$$

Thus, estimating the at least one radiographic magnification factor may comprise estimating a magnification factor relating to at least one anatomical structure used in registering the two and three dimensional radiographic images, such as the vertebrae. The magnification factor relating to the lungs may in turn be derived on the basis of the magnification factor relating to the at least one anatomical structure.

In some examples, the vertebra magnification factor may be calculated either as a global magnification factor (e.g. by taking the result of a single vertebra or the average of several vertebrae) or a spatially-varying magnification factor which varies along the cranio-caudal direction by interpolating the magnification factors determined for different vertebrae.

Distances as described herein, such as the source-lung distances, lung-detector distances, lung-anatomy distances, and so on, may be calculated using a 3D model constructed using the determined projection geometry data. The 2D/3D registration allows the positions and orientations of objects such as the source, detector, and anatomy to be described within a single coordinate system, such that interobject distances may readily be determined. When calculating distances to or from anatomical structures, midplanes or centre points of those structures may be taken as the point of reference, for example a centre point of a lung may be used in calculating distances from the source or detector to that lung.

Once the magnification factor has been determined, any appropriate method may be used to estimate the lung volume based thereon. In one example, in which the lung volume estimation is based on a lung area determined from the 2D image, the magnification factor for the lung or lungs may be used to scale down the lung area before using the scaled-down lung area to estimate lung volume. In other words, calculating the estimated lung volume comprises using at least one lung magnification factor to scale a lung area determined using the two dimensional radiographic image. In the case that separate magnification factors are estimated for the left and right lungs, these may be used to scale down the area of the respective lung before lung volume is estimated. That is, the method may comprise scaling lung areas of the left and right lungs separately using respective magnification factors determined for the left and right lungs. Thus, different scaling might apply to the left and right lungs. The lung area may be scaled according to $1/M^2$, where M is the magnification factor of the respective lung. Calculating the estimated lung volume may comprise integrating pixel intensity values over the scaled lung area. Equally, the magnification factor may be used to scale volumes calculated for individual pixels, or summations thereof, or a water equivalent path length.

In one example, calculating the estimated lung volume may comprise estimating, for each pixel in a lung area of the 2D image, a volume that contributed to its intensity value.

That volume may be approximately equal to the water equivalent path length times the pixel size, corrected additionally for the magnification. More particularly, that volume may be estimated as $V=lS/M^2$, where l is the water equivalent path length, S is the pixel size, and M is the magnification factor for the lung in question. The water equivalent path length may be estimated using any appropriate known method.

To account for the local inclination angle of x-rays onto the detector, estimating the volume for each pixel may comprise determining an effective pixel size to use in the above calculation in place of the actual pixel size. If the ray hits the detector perpendicularly, then the effective pixel size $S_{\textit{eff}}$ may be taken to be equal to the physical pixel size S. Otherwise, for an inclination angle $\alpha \neq 90°$, the (smaller) effective pixel size may be used, namely $S_{\textit{eff}}=S\cos(90°-\alpha)$. The inclination angle for each pixel may be determined using the above-mentioned 3D model.

In another example, calculating the estimated lung volume comprises: segmenting the two dimensional radiographic image to identify the left and right lungs; modifying the two dimensional radiographic image to replace image data in a region corresponding to the left and right lungs with predefined pixel intensity values, thereby forming a thorax mask image; and subtracting the thorax mask image from the original two dimensional radiographic image to form a lungs-only image providing lung volume information. The predefined values may correspond to expected pixel intensity values for soft tissue or water, for example. Calculating the estimated lung volume may further comprise integrating pixel intensity values over the lungs-only image based on a known correlation between the area and intensity of the pixels in the region corresponding to the left and right lungs and the total lung volume. The area over which intensity values are integrated may be the scaled-down lung area determined based on the magnification factor for the lung or lungs.

According to a second aspect, there is provided a computing system configured to perform any of the methods described herein.

According to a third aspect, there is provided a computer program product comprising instructions which, when executed by a computing system, enable or cause the computing system to perform any of the methods described herein.

According to a fourth aspect, there is provided a computer-readable medium comprising instructions which, when executed by a computing system, enable or cause the computing system to perform any of the methods described herein.

Systems and methods disclosed herein provide for improved lung volume estimation from radiographies. Estimating the lung volume accurately provides valuable quantitative information about the state of patients in the ICU. However, quantitative evaluation requires knowledge about the system geometry and the positioning of the patient inside the system, which is usually not available in the ICU setting using mobile x-ray systems. According to the present disclosure, this problem is overcome by estimating the projection geometry by using previously acquired CT data.

The "two-dimensional radiographic image" as described herein may comprise an x-ray image or radiograph, in particular a projectional radiograph, and more particularly one captured using a mobile detector, for example a flat-panel detector. The two-dimensional radiographic image as a planar image comprises an array of pixels representing the spatial intensity distribution of the incident x-rays.

The "three-dimensional radiographic image" as described herein may comprise for example a computed tomography (CT) image or radiograph which, as a volumetric image, comprises a volume of voxels representing the spatial intensity distribution.

The invention may include one or more aspects, examples or features in isolation or combination whether or not specifically disclosed in that combination or in isolation. Any optional feature or sub-aspect of one of the above aspects applies as appropriate to any of the other aspects.

These and other aspects of the invention will be apparent from and elucidated with reference to the embodiments described hereinafter.

BRIEF DESCRIPTION OF THE DRAWINGS

A detailed description will now be given, by way of example only, with reference to the accompanying drawings, in which:—

FIGS. 4A-D illustrate the formation of difference images as part of one example of 2D/3D image registration;

DETAILED DESCRIPTION OF EMBODIMENTS

Figure 1:
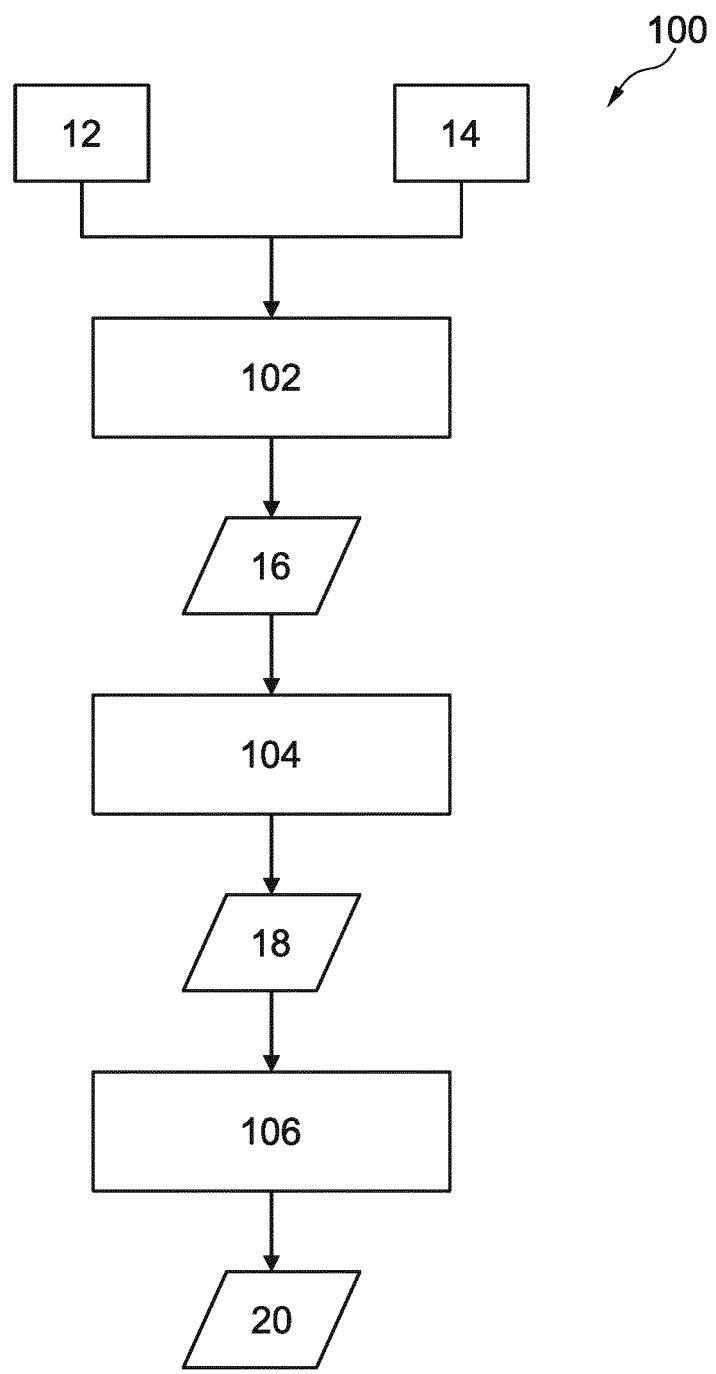
FIG. 1 is a flowchart illustrating a method of estimating lung volume from radiographic images.

According to the present disclosure, lung volume estimation can be improved by estimating the projection geometry using a previously acquired CT image, in particular by estimating the magnification factor applying to the x-ray imaging setup using a 2D-3D registration of parts of the pre-acquired CT image. Often, such a chest CT image is available for patients entering the ICU. FIG. 1 is a flowchart illustrating a method 100 of estimating lung volume from radiographic images according to the present disclosure. Broadly speaking, the method 100 comprises the following steps. In a first step 102, a two dimensional radiographic image 12 and a three dimensional radiographic image 14 of the patient's chest are received, the two dimensional radiographic image 14 having been captured using unknown projection geometry, and the two images 12, 14 are registered to estimate the projection geometry 16. In a second step 104, the projection geometry 16 is used to estimate at least one radiographic magnification factor 18 relating to an imaging setup used to capture the two dimensional radiographic image 12. In a third step 106, an estimated lung volume 20 is calculated using the two dimensional radiographic image 12 and the at least one radiographic magnification factor 18.

FIGS. 2A-F illustrate aspects of the method of FIG. 1.

Figure 2A:
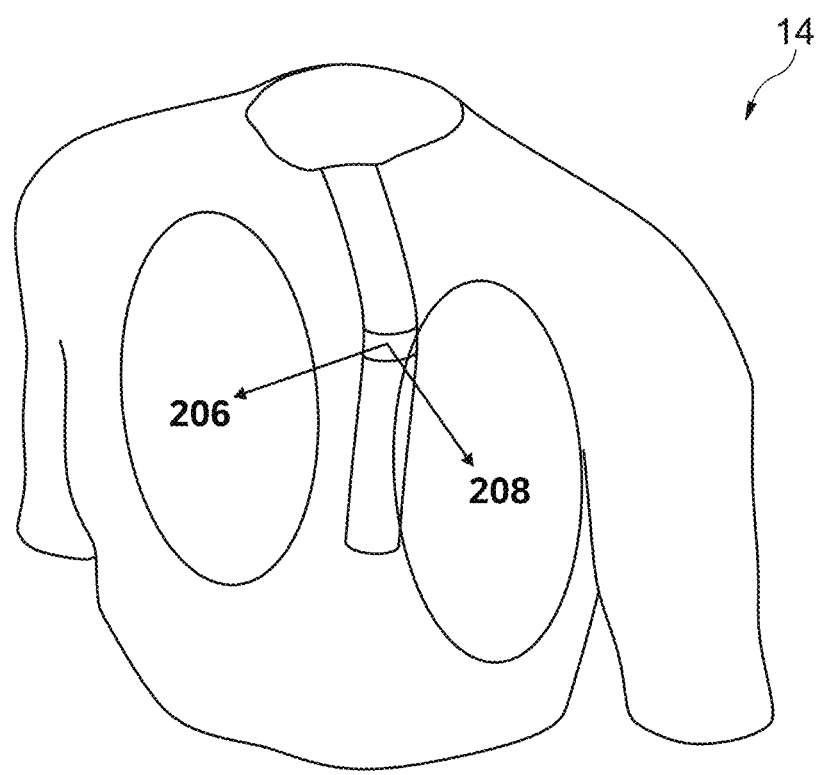
FIGS. 2A-F illustrate aspects of the method of FIG. 1.

FIG. 2A shows a 3D image 14 of the patient's chest. The 3D image 14 is a CT image which has been segmented to identify relevant anatomical structures, in this case the spine and the lungs. In particular, the sixth thoracic vertebra is identified. The segmentation provides also 3D relative positions of relevant anatomical structures. For instance, the arrows 208 and 206 shown in FIG. 2A point from the centre of the sixth thoracic vertebra to the centres of the left and right lungs, respectively.

Figure 2B:
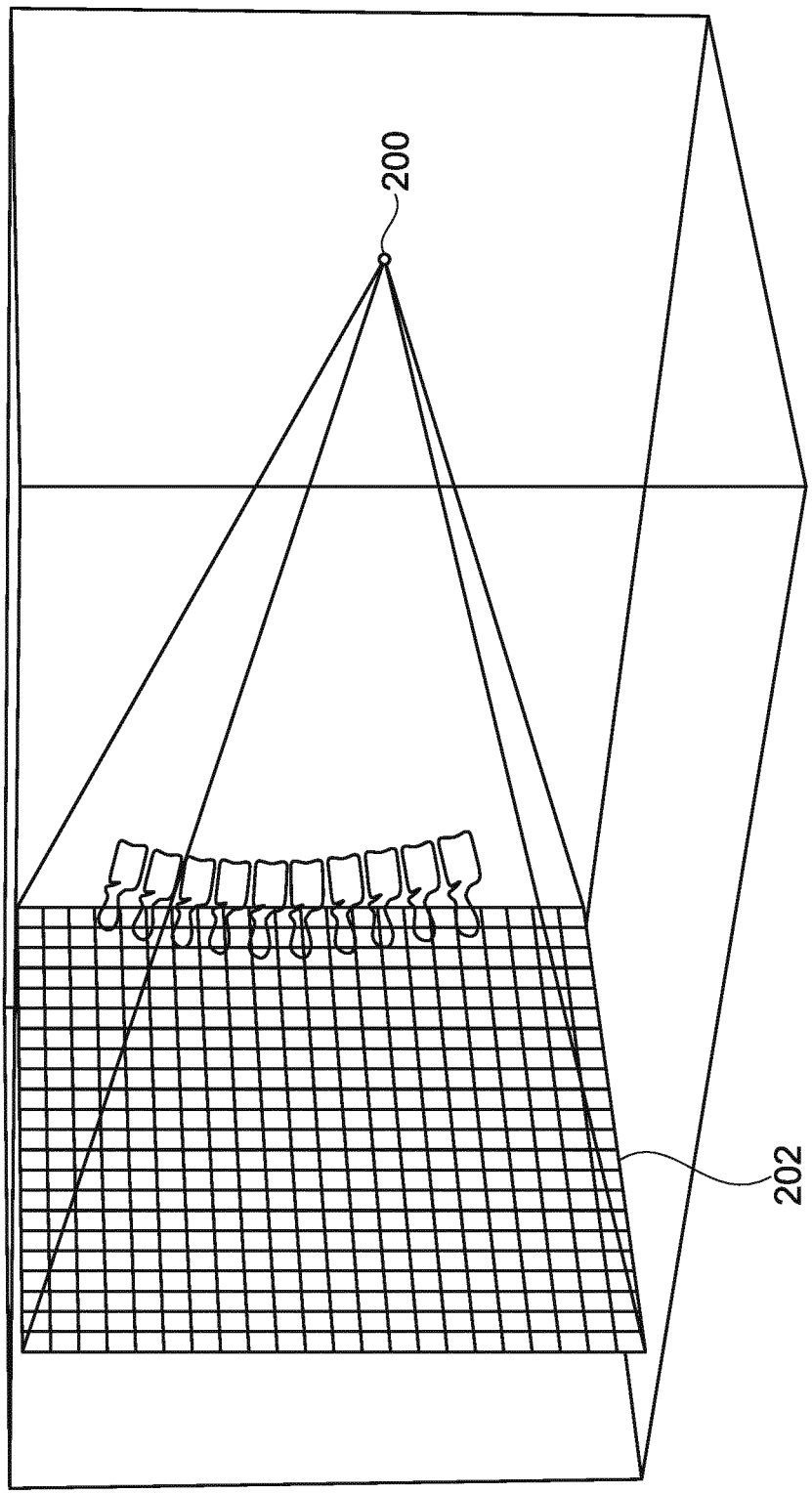

FIG. 2B illustrates the estimation of the projection geometry 16 by means of a 2D/3D registration of the images with respect to the sixth thoracic vertebra. The projection geometry data includes values for nine parameters that uniquely describe the position of the x-ray source 200 as well as the position and orientation of the x-ray detector 202 in the vertebra-centric coordinate system.

Figure 2C:
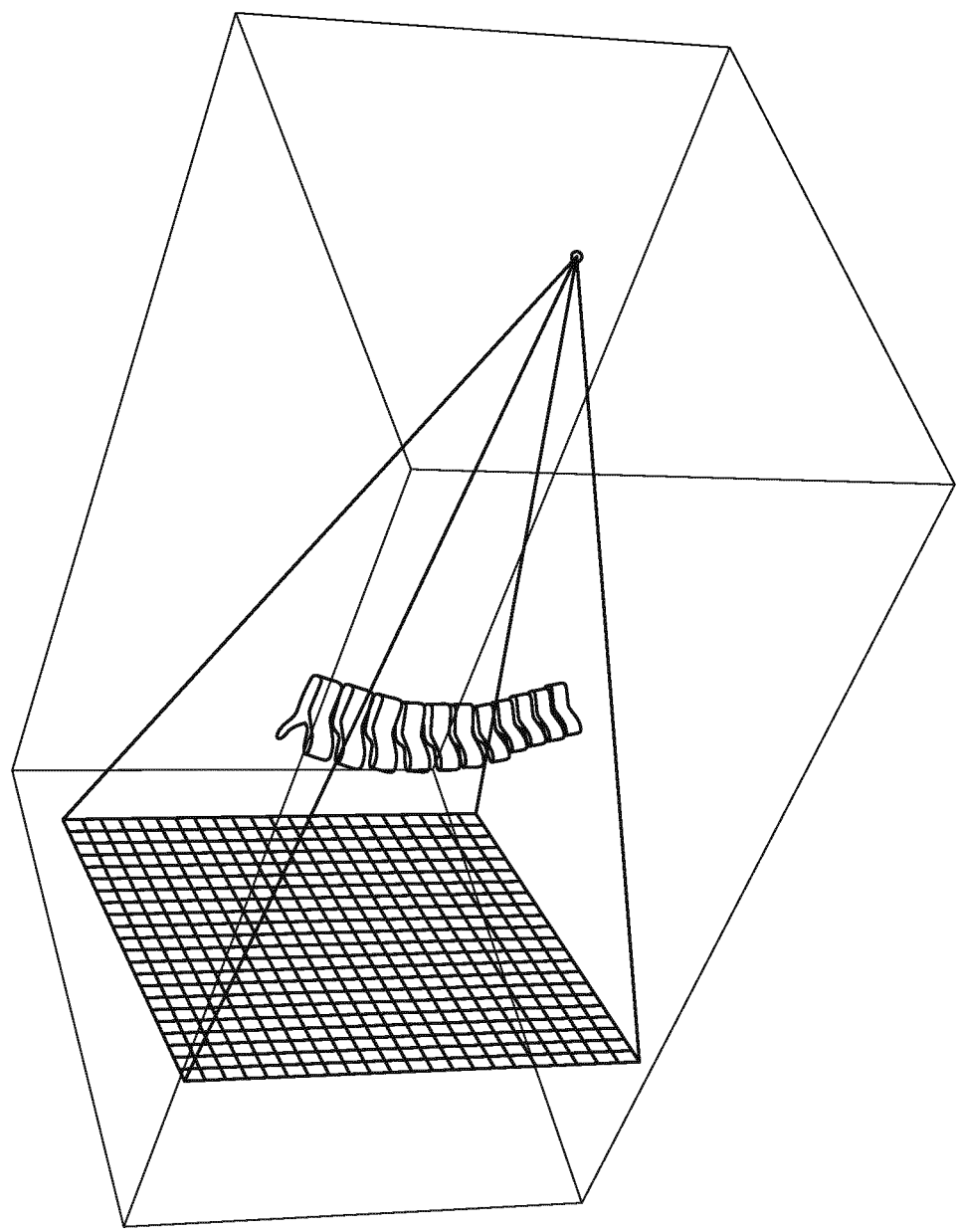

FIG. 2C illustrates an optional step of performing inclination correction to account for the effect that rays with non-perpendicular incident angles have on the effective pixel size. The effective pixel size $S_{eff}$ depends on the local inclination angle of the ray onto the detector 202. If the ray hits the detector 202 perpendicularly, then the effective pixel size $S_{eff}$ is equal to the physical pixel size S. For an inclination angle $\alpha \neq 90°$, the effective pixel size is smaller, namely $S_{eff}=S \cos(90°-\alpha)$. The following computations may thus optionally use the effective pixel size in place of the physical pixel size to perform inclination correction.

Figure 2D:
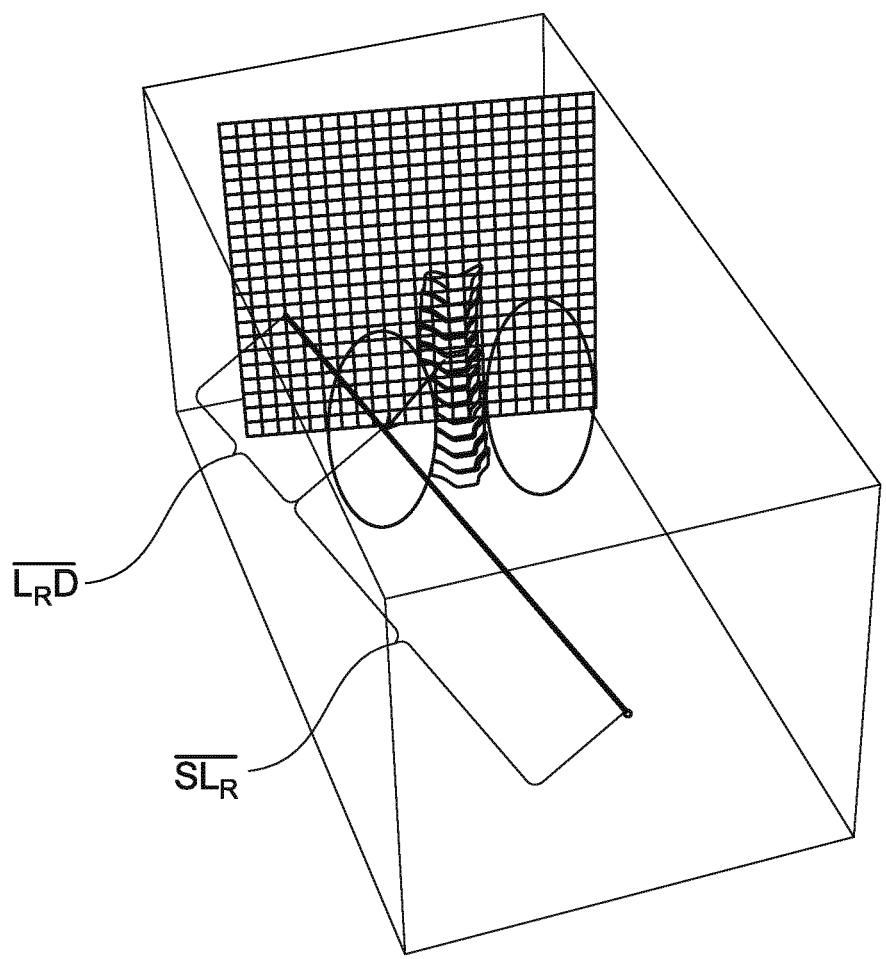
Figure 2E:
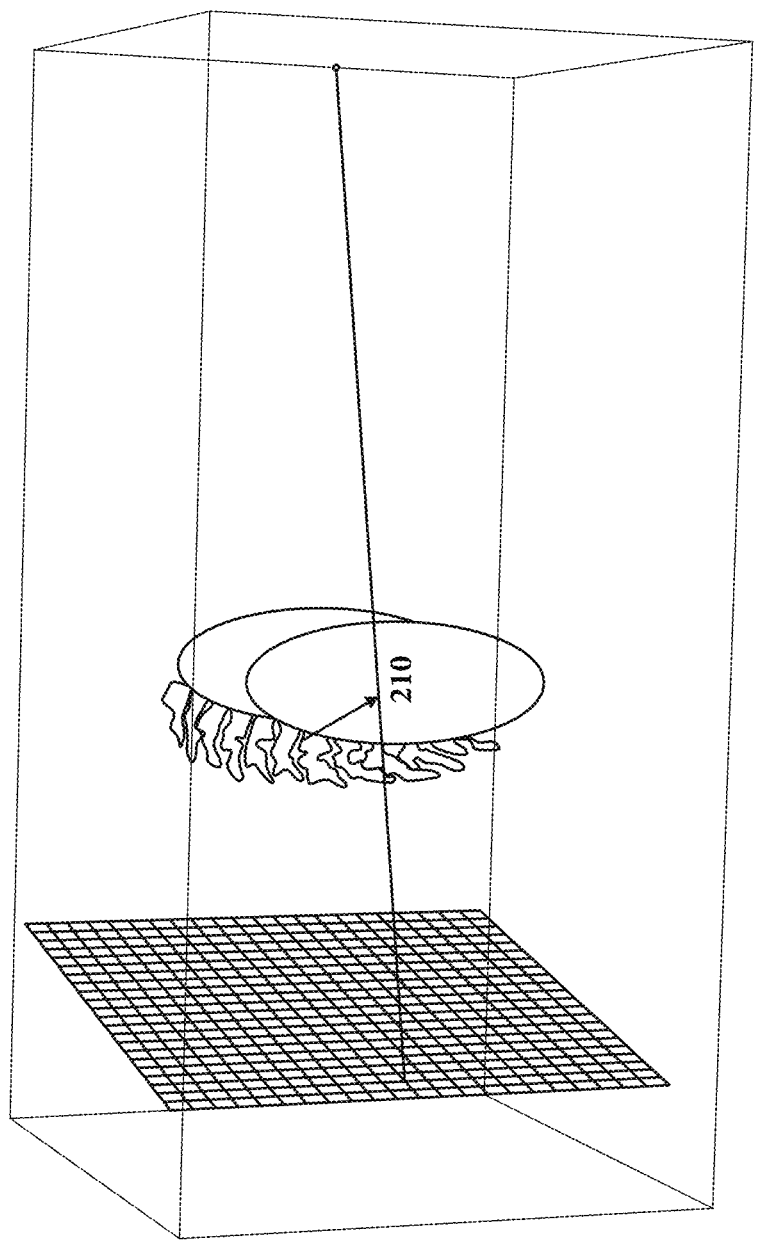

FIG. 2D illustrates the estimation of a magnification factor 18 in step 104. As mentioned above, following the 2D-3D registration, the positions of the centres of the left and right lungs relative to the centre of the sixth thoracic vertebra are known. Using that information, the distance from the source 200 to the centre of the right lung ($\overline{SL_R}$) and the distance from the centre of the right lung to the detector 202 ($\overline{L_R D}$) are calculated. The magnification factor of the right lung $M_{L_R}$ (that is, of the centre of the right lung 210 in FIG. 2E) is estimated as $$M_{L_R} = \frac{\overline{SL_R}}{\overline{SL_R} + \overline{L_R D}}.$$

In the case that the detector 202 is not inclined, the magnification factor of the right lung may also be taken as the magnification factor of the left lung. Otherwise, in the case that the detector 202 is inclined or slanted, as shown more clearly in FIG. 2E, the magnification may be different for the left and right lungs, and so per-lung magnification factors may be estimated using the above-described technique.

Figure 2F:
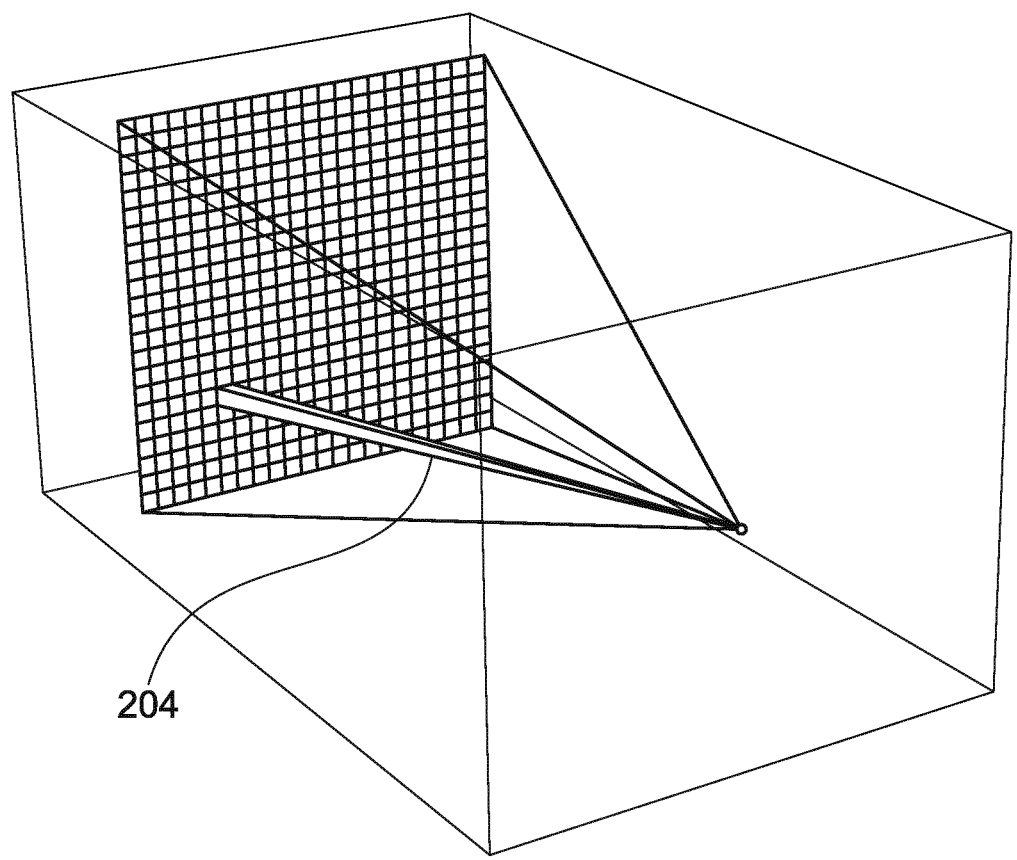

FIG. 2F illustrates the estimation of the lung volume 20 in step 106. Firstly, the water equivalent path length through the lung is estimated, as is known in the art. The next step is to estimate for each pixel the volume that contributed to its value. This volume is approximately equal to the water equivalent path length times the effective pixel size corrected additionally for the magnification. FIG. 2F shows the volume 204 that contributes to the value measured by one particular pixel of the detector 202. The estimated water length corresponds to a larger volume if the corresponding volume is close to the detector. The estimated volume V corresponding to an estimated water length l is then calculated as $V=lS_{eff}/M^2$. Volumes estimated for individual pixels in this way are summed over the lung area in the 2D image 12 to estimate the lung volume 20 for one or both of the lungs.

Returning to step 102, one example of registration of the 2D and 3D images 12, 14 to estimate the projection geometry 16 will now be described. In this example, the 2D image 12 is a recent x-ray image of a patient's chest which is to be processed to estimate current lung volume and the 3D image 14 is a pre-acquired CT image of the patient's chest captured when the patient first entered the ICU. The registration is performed with respect to one or more vertebrae, which represent the anatomical structure serving as the object of interest. By registering the x-ray image 12 to the CT image 14, the position of the vertebrae in the x-ray imaging setup may be estimated. The following example of a suitable 2D/3D image registration process is based on that described in WEESE et al. Voxel-based 2-D/3-D Registration of Fluoroscopy Images and CT Scans for Image-guided Surgery. In: IEEE Transaction on Information Technology in Biomedicine, 1(4). 1997.

Figure 3:
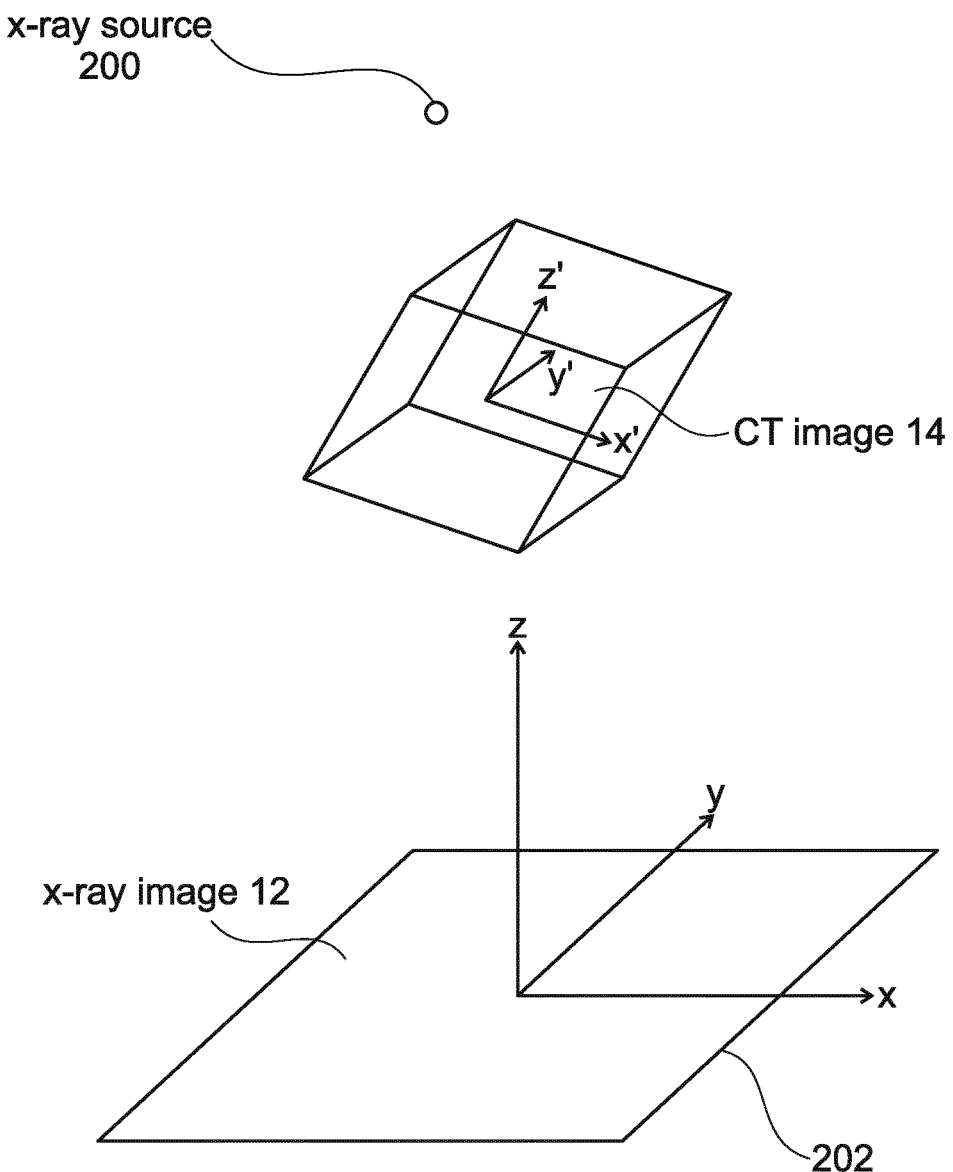
FIG. 3 illustrates projection geometry in an x-ray imaging setup.

FIG. 3 illustrates the projection geometry. The x-ray image 12 was captured using the x-ray source 200 and the mobile x-ray detector 202 residing in a projection plane. The x-ray image 12 is associated with a coordinate system (x,y,z) whose origin exists in the centre of the x-ray image 12. The projection plane lies in the x-y plane of the coordinate system such that the source 200 is located above the projection plane in the z-direction. The CT image 14 has its own coordinate system (x',y',z') having its origin in the centre of the CT image 14, which may also be the centre of a particular vertebra following image segmentation. The location and orientation of the CT image 14 with respect to the coordinate system of the x-ray image 12 can be described by the transformation x=R($\omega$)x'+t, wherein R($\omega$) is a rotation matrix corresponding to the rotation vector $\omega=(\omega_x, \omega_y, \omega_z)$ computed as follows:

$$R(\omega)x = x + \frac{\sin\alpha}{\alpha}\omega \times x + \frac{1-\cos\alpha}{\alpha^2}\omega \times (\omega \times x),$$

where $\alpha=\sqrt{\omega_x^2+\omega_y^2+\omega_z^2}$, and t is the translation vector $t=(t_x, t_y, t_z)$.

The 2D/3D registration algorithm determines the transformation parameters $\omega$ and t given starting estimates $\omega_0$ and $t_0$ by performing the following steps.

1) Segmentation of the vertebra of interest in the CT image 14.
2) Subtraction of the average grey value of the tissue around the vertebra from the CT image 14.
3) Computation of a reconstructed 2D image from the CT image 14 using the current values of the rotation and translation parameters $\omega$ and t, taking only the CT volume with the segmented vertebra into account. Since the average grey value of the tissue directly adjacent to the vertebra has been subtracted from the CT image 14, the reconstructed 2D image shows the grey-value variation due to the presence of the vertebra only.
4) Scaling of the grey values in the reconstructed 2D image with a predetermined scaling factor $I_0$ and subtraction from the x-ray image 12 to form a difference image. For a proper grey-value scaling and the correct location and orientation of the CT image 14, the structures in the x-ray image 12 corresponding to the vertebra will vanish and overall there will be less structure visible after subtraction. FIG. 4A shows one example of an x-ray image 12 of the patient's spine, while FIGS. 4B-D show three difference images 402-406 formed by subtraction of 2D images reconstructed from CT volumes respectively for three different segmented vertebrae. Disappearance of the respective vertebra in the difference images 302-306 indicates proper determination of the transformation parameters.

5) Calculation of a similarity metric that characterizes the structuredness of the difference image formed after subtraction of the grey-value-scaled reconstructed 2D image.
6) Optimization of the similarity metric, with respect to the grey-value scaling factor $I_0$ and the parameters $\omega$ and t.

Within each iteration of the optimization, steps 3)-5) are repeated. The transformation parameters are varied according to a predetermined sequence, for example, $t_x$, $t_y$, $t_z$, $\omega_x$, $\omega_y$, $\omega_z$. The optimization is carried out repeatedly until a predetermined number of subsequent maximizations, e.g. six, do not further increase the similarity metric. The grey-value scaling factor $I_0$ may be adjusted whenever one of the other parameters is changed, by varying the factor between zero and a maximal value with a predefined increment. Maximization with respect to a single parameter may be performed using an adjustable step size $\Delta$. The step size $\Delta$ is increased ($N_{limit}\Delta \to \Delta$), if $N_{limit}$ successive steps in the same direction increase the similarity measure. If neither a step forward nor a step backward increases the similarity measure, the step size $\Delta$ is reduced as long as it is larger than a minimum value $\Delta_{min}$ ($\max(\Delta/N_{limit}, \Delta_{min}) \to \Delta$). For each parameter, separate values of the step size $\Delta$ and the minimum step size $\Delta_{min}$ are used. At the beginning of the optimization, the step size $\Delta$ is initialized by a multiple of its minimum value $\Delta_{min}$.

The similarity metric characterizing the structuredness may be implemented using a function of the difference image which assigns a value approaching zero to points in the neighbourhood of structures, such as grey-value edges or lines and values around unity to points in areas showing only little grey-value variation. In one non-limiting example, the function is defined according to $$P_{r,\sigma}(I_{diff}) = \sum_{x,y} \sum_{(x-v)^2+(y-w)^2 \leq r^2} \frac{\sigma^2}{\sigma^2 + (I_{diff}(x,y) - I_{diff}(v,w))^2},$$

where $I_{diff}$ denotes the difference image, r denotes a parameters indicating the size of the neighbourhood in which grey-value indications are taken into account, and $\sigma$ represents a sensitivity adjustment controlling whether a grey-value variation is considered to relate to a structure. It will be noted that the first sum runs over all pixels x,y. The second sum runs over all pixels v, w with $(x-v)^2+(y-w)^2 < r^2$.

A further example of performing 2D-3D image registration by geometrically determining pose parameters using landmarks is described in YANG, H. et al. "Geometry calibration method for a cone-beam CT system". Med. Phys. 44(5), May 2017. p. 1692-1706.

Figure 5A:
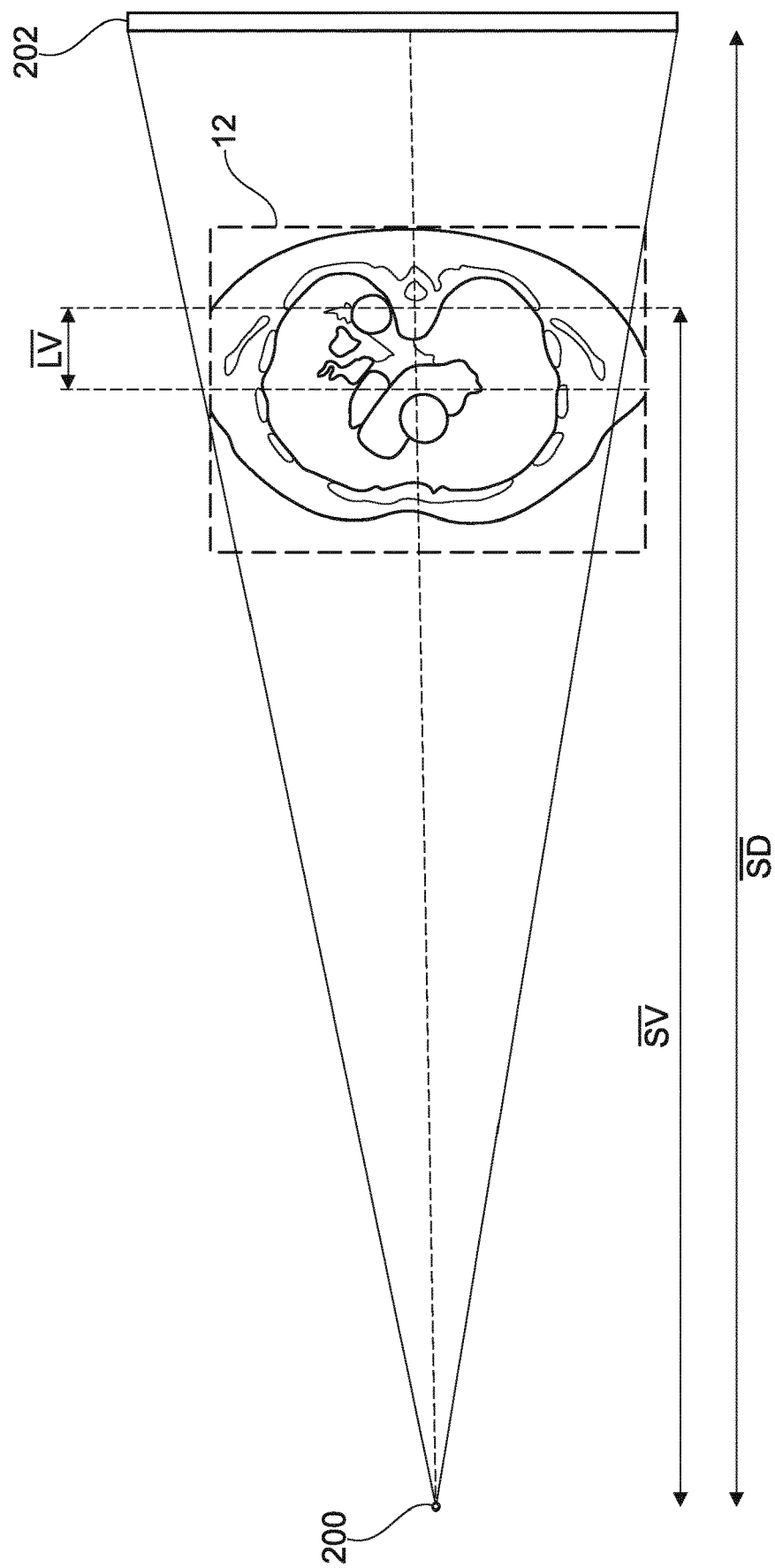
FIGS. 5A-B illustrate exemplary methods for estimating lung magnification factors using determined projection geometry.

FIG. 5A illustrates a further exemplary method for estimating the lung magnification factor 20 using the determined projection geometry 16 for a patient in a supine position. The magnification factor for the lungs is calculated as $$M_L = \frac{\overline{SD}}{\overline{SV} - \overline{LV}}.$$

A magnification factor tor the vertebra may be calculated as $$M_V = \frac{\overline{SD}}{\overline{SV}}.$$

Figure 5B:
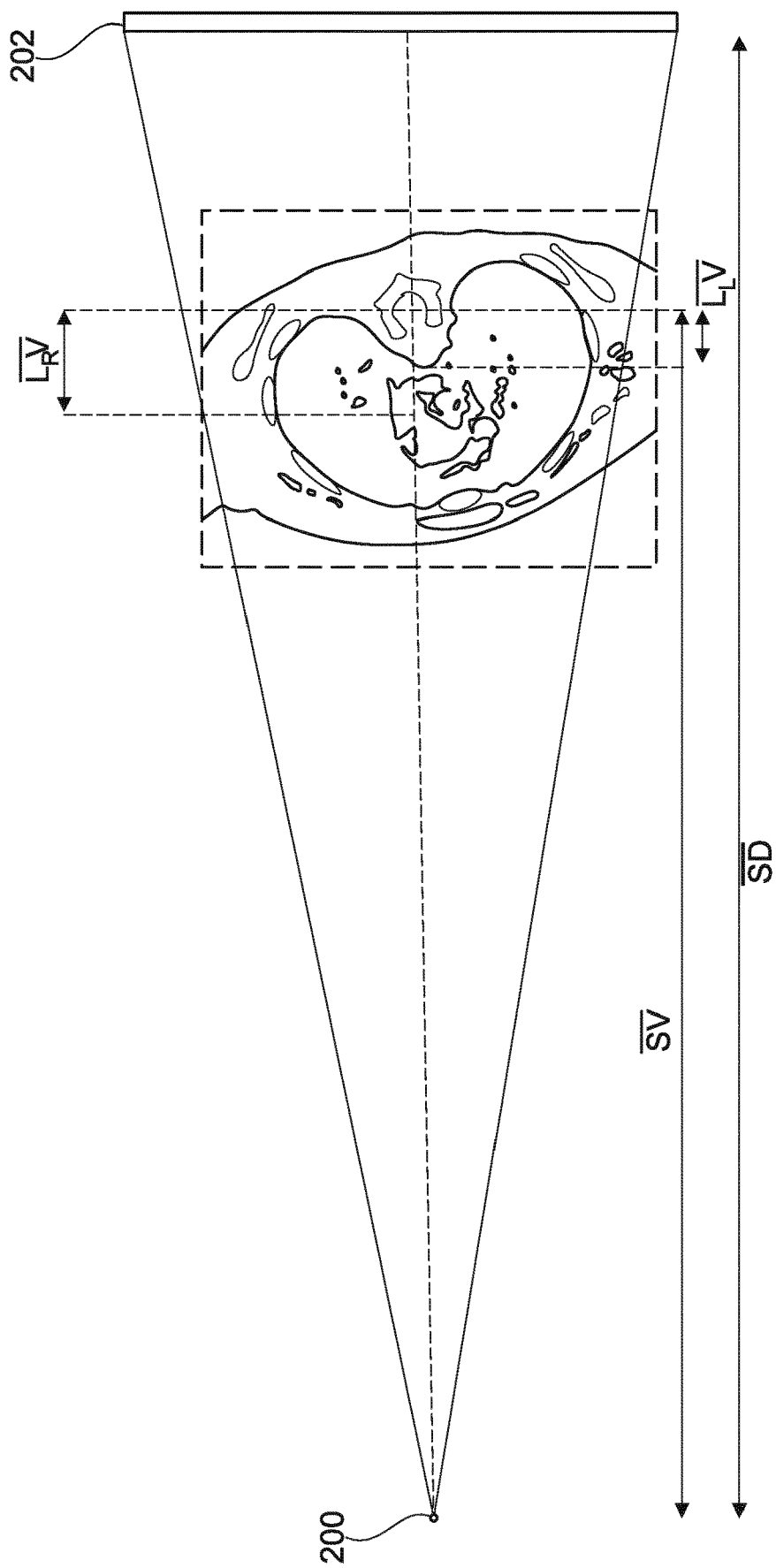

FIG. 5B illustrates another exemplary method for estimating the lung magnification factor 20 using the determined projection geometry 16 for a patient in an oblique position. In this example, separate lung-vertebra distances $\overline{L_L V}$ and $L_R V$ for the left and right lungs substitute for $\overline{LV}$ in the above equation to calculate per-lung magnification factors.

Figure 6:
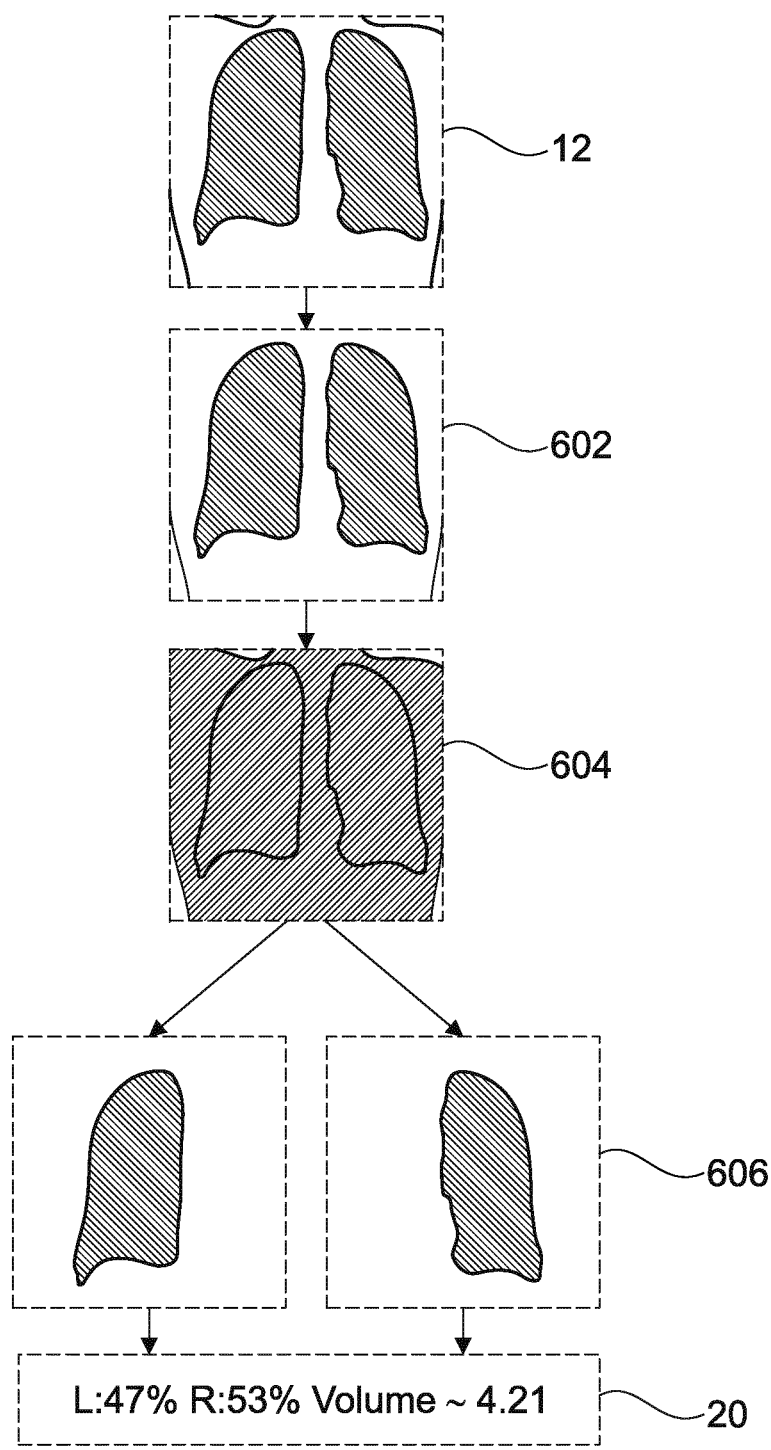
FIG. 6 illustrates a further exemplary method for performing lung volume estimation.

FIG. 6 illustrates a further exemplary method for performing the lung volume estimation. Using the x-ray image 12 of the patient's chest, a lungs mask image 602 is formed after segmenting the x-ray image 12 to identify the left and right lungs. Then, the lungs mask image 602 is used to modify the x-ray image 12 so as to replace image data in the region identified as belonging to the left and right lungs with expected pixel intensity values for soft tissue, thereby forming a thorax mask image 604. The thorax mask image 604 is subtracted from the x-ray image 12 to form a lungs-only image 606. At any point after the lungs are identified, the lung area is scaled using the magnification factor or factors determined for the lungs. The lung volume 20 is estimated by integrating pixel intensity values in the lungs-only image 606 over the scaled lung area.

Other suitable methods for estimating lung volume are described in more detail for example in U.S. Pat. No. 9,805,467 B2 or US 2018/0271465 A1.

Figure 7:
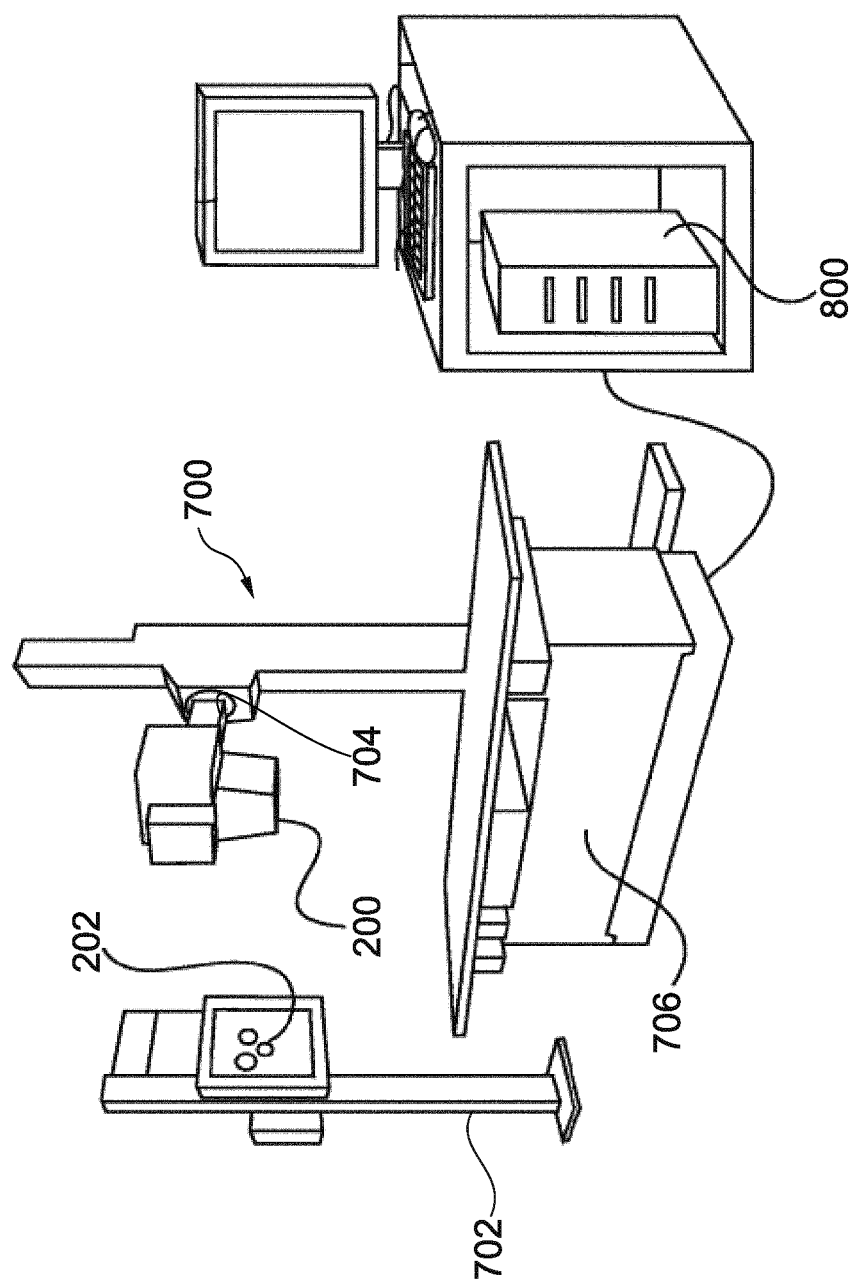
FIG. 7 shows an x-ray imaging setup which may be used to capture an x-ray image.

FIG. 7 shows an x-ray imaging setup 700 which may be used to capture the x-ray image 12. The x-ray source 200 is repositionable to face the portable x-ray detector 202. In the illustrated example, the detector 202 is mounted on a stand 702, while the source 200 is provided on a rotatable mounting 704 to enable it to be swivelled into a horizontal position and aimed towards the stand-mounted detector 202, for imaging of the patient in a standing position. Alternatively, the imaging may be performed with the patient lying on the bed 706, and with the detector 202 positioned on or under the bed 706. The x-ray image 12 is received by a computing system 800, described further below, for processing according to the methods described herein.

Numerous variations to the systems and methods described herein may be envisaged. For example, although the above-described examples relate to the use of vertebrae to generate the correspondence between the x-ray image 12 and the CT image 14, other anatomical structures such as bones can in principle be used, in particular the ribs.

Alternative approaches to 2D/3D registration may be used, such as those based on contours.

The invention applies generally to mobile x-ray, for example to use in the ICU where the clinical need may be strongest, but is not so limited. The invention is also applicable to quantitative dark-field x-ray imaging, where the lung volume estimation is used to estimate quantitative information on the lung structure.

Figure 8:
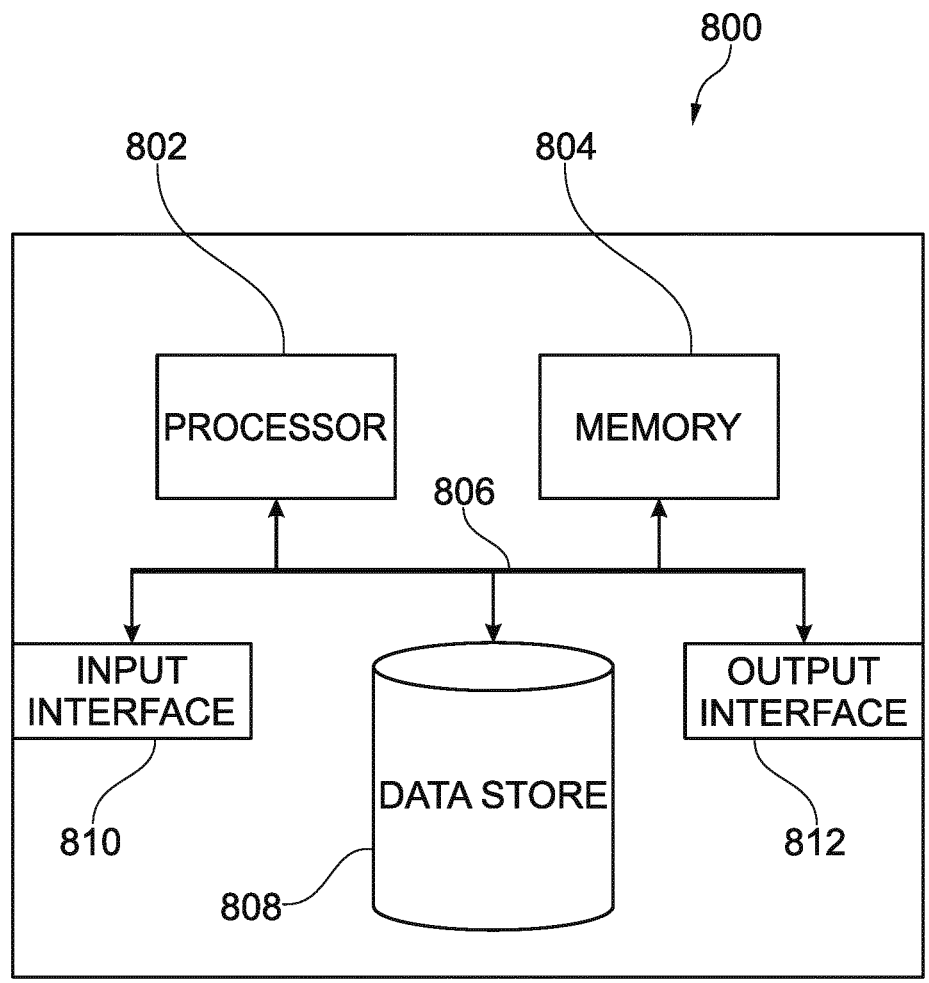
FIG. 8 illustrates a computing system that can be used in accordance with the systems and methods disclosed herein.

FIG. 8 illustrates an exemplary computing system 800 that can be used in accordance with the systems and methods disclosed herein. The computing system 800 may form part of or comprise any desktop, laptop, server, or cloud-based computing system. The computing system 800 includes at least one processor 802 that executes instructions that are stored in a memory 804. The instructions may be, for instance, instructions for implementing functionality described as being carried out by one or more components described herein or instructions for implementing one or more of the methods described herein. The processor 802 may access the memory 804 by way of a system bus 806. In addition to storing executable instructions, the memory 804 may also store conversational inputs, scores assigned to the conversational inputs, etc.

The computing system 800 additionally includes a data store 808 that is accessible by the processor 802 by way of the system bus 806. The data store 808 may include executable instructions, log data, etc. The computing system 800 also includes an input interface 810 that allows external devices to communicate with the computing system 800. For instance, the input interface 810 may be used to receive instructions from an external computer device, from a user, etc. The computing system 800 also includes an output interface 812 that interfaces the computing system 800 with one or more external devices. For example, the computing system 800 may display text, images, etc. by way of the output interface 812.

It is contemplated that the external devices that communicate with the computing system 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing system 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing system 800 may be a distributed system. Thus, for instance, several devices may be in communication by way of a network connection and may collectively perform tasks described as being performed by the computing system 800.

Various functions described herein can be implemented in hardware, software, or any combination thereof. If implemented in software, the functions can be stored on or transmitted over as one or more instructions or code on a computer-readable medium. Computer-readable media include computer-readable storage media. Computer-readable storage media can be any available storage media that can be accessed by a computer. By way of example, and not limitation, such computer-readable storage media can comprise FLASH storage media, RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

It will be appreciated that the aforementioned circuitry may have other functions in addition to the mentioned functions, and that these functions may be performed by the same circuit.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features.

It has to be noted that embodiments of the invention are described with reference to different categories. In particular, some examples are described with reference to methods whereas others are described with reference to apparatus. However, a person skilled in the art will gather from the description that, unless otherwise notified, in addition to any combination of features belonging to one category, also any combination between features relating to different category is considered to be disclosed by this application. However, all features can be combined to provide synergetic effects that are more than the simple summation of the features.

While the invention has been illustrated and described in detail in the drawings and foregoing description, such illustration and description are to be considered exemplary and not restrictive. The invention is not limited to the disclosed embodiments. Other variations to the disclosed embodiments can be understood and effected by those skilled in the art, from a study of the drawings, the disclosure, and the appended claims.

The word "comprising" does not exclude other elements or steps.

The indefinite article "a" or "an" does not exclude a plurality. In addition, the articles "a" and "an" as used herein should generally be construed to mean "one or more" unless specified otherwise or clear from the context to be directed to a singular form.

A single processor or other unit may fulfil the functions of several items recited in the claims.

The mere fact that certain measures are recited in mutually different dependent claims does not indicate that a combination of these measures cannot be used advantageously.

A computer program may be stored/distributed on a suitable medium, such as an optical storage medium or a solid-state medium supplied together with or as part of other hardware, but may also be distributed in other forms, such as via the internet or other wired or wireless communications systems.

Any reference signs in the claims should not be construed as limiting the scope.

Unless specified otherwise, or clear from the context, the phrases "one or more of A, B and C", "at least one of A, B, and C", and "A, B and/or C" as used herein are intended to mean all possible permutations of one or more of the listed items. That is, the phrase "X comprises A and/or B" is satisfied by any of the following instances: X comprises A; X comprises B; or X comprises both A and B.

The invention claimed is:

1. A computer-implemented method of estimating lung volume from radiographic images, the method comprising:
   registering a two dimensional radiographic image of a patient's chest to a three dimensional radiographic image of the patient's chest to estimate data describing projection geometry of an imaging setup used to capture the two dimensional radiographic image;
   using the projection geometry to estimate at least one radiographic magnification factor relating to the imaging setup; and
   calculating an estimated lung volume using the two dimensional radiographic image and the at least one radiographic magnification factor.

2. The method of claim 1, wherein the registering comprises using at least one trained machine learning model to register the two dimensional radiographic image to the three dimensional radiographic image to estimate the data describing the projection geometry.

3. The method of claim 1, wherein the registering comprises forming a sub-image from one or both of the two and three dimensional radiographic images before performing the registration, the sub-image depicting at least one anatomical structure to be used in the registration.

4. The method of claim 3, wherein forming the sub-image comprises segmenting respective radiographic image to isolate at least one anatomical structure.

5. The method of claim 1, wherein the registering comprises using an iterative registration algorithm which repeatedly makes incremental changes to an estimated projection geometry and calculates a correlation metric between the two images being registered using the incrementally-changed projection geometry until the correlation metric converges to a steady state value.

6. The method of claim 5, wherein the correlation metric comprises a similarity metric which describes the structuredness of a difference image which is obtained by subtracting one of the two images being registered from the other.

7. The method of claim 1, comprising using at least a source-lung distance for a lung to estimate the at least one radiographic magnification factor for the lung.

8. The method of claim 7, comprising calculating the magnification factor for the lung as the ratio of the source-lung distance over a source-detector distance.

9. The method of claim 1, comprising estimating the at least one magnification factor differently according to whether the patient is in a supine or prone position.

10. The method of claim 1, wherein calculating the estimated lung volume comprises estimating, for each pixel in a lung area of the two-dimensional radiographic image, a volume that contributed to its intensity value.

11. The method of claim 10, comprising estimating the volume on the basis of water equivalent path length times pixel size, corrected using the at least one estimated magnification factor.

12. The method of claim 11, comprising determining the pixel size as an effective pixel size which accounts for non-perpendicular x-ray incident angles.

13. The method of claim 1, wherein calculating the estimated lung volume comprises separately using respective magnification factors determined for the left and right lungs.

14. A computing system configured to perform the method of claim 1.

* * * * *